(12) United States Patent
Brunfeld et al.

(10) Patent No.: US 7,214,932 B2
(45) Date of Patent: May 8, 2007

(54) RESONATOR METHOD AND SYSTEM FOR DISTINGUISHING CHARACTERISTICS OF SURFACE FEATURES OR CONTAMINANTS

(75) Inventors: Andrei Brunfeld, Cupertino, CA (US); Gregory Toker, Jerusalem (IL); Bryan Clark, Mountain View, CA (US)

(73) Assignee: Xyratex Technology Limited, Havant, Hampshire (GB)

( * ) Notice: Subject to any disclaimer, the term of this patent is extended or adjusted under 35 U.S.C. 154(b) by 29 days.

(21) Appl. No.: 11/167,807

(22) Filed: Jun. 27, 2005

(65) Prior Publication Data

US 2005/0236589 A1  Oct. 27, 2005

Related U.S. Application Data

(63) Continuation-in-part of application No. 10/750,747, filed on Jan. 2, 2004, now Pat. No. 6,879,421.

(60) Provisional application No. 60/583,343, filed on Jun. 28, 2004.

(51) Int. Cl.
  *H01J 3/14* (2006.01)
  *H01J 40/14* (2006.01)
  *H01J 5/16* (2006.01)

(52) U.S. Cl. ............ 250/234; 250/559.4; 250/216; 356/450

(58) Field of Classification Search ........... 250/201.5, 250/216, 234–236, 559.11, 559.22, 559.4, 250/559.45; 359/237–324; 356/5.05, 450, 356/237.2, 479, 502, 519
See application file for complete search history.

(56) References Cited

U.S. PATENT DOCUMENTS 5,235,192 A * 8/1993 Chase et al. .......... 250/559.11
6,522,471 B2    2/2003 Clark
6,653,649 B2 * 11/2003 Clark ................ 250/559.11
6,700,840 B2    3/2004 Clark
6,714,295 B2 * 3/2004 Clark ................ 356/237.2

(Continued)

OTHER PUBLICATIONS

U.S. Appl. No. 11/143,018, filed Jun. 1, 2005, Brunfeld, et al.

(Continued)

*Primary Examiner*—Georgia Epps
*Assistant Examiner*—Patrick J. Lee
(74) *Attorney, Agent, or Firm*—Mitch Harris, Atty at Law, LLC; Andrew M. Harris

(57) ABSTRACT

A resonator method and system for distinguishing characteristics of surface features or contaminants provides improved inspection or surface feature detection capability in scanning optical systems. A resonator including a surface of interest in the resonant path is coupled to a detector that detects light leaving the resonator. Changes in the resonance peak positions and peak intensities are evaluated against known changes for standard scatters in order to determine the material characteristics of an artifact at the surface of interest that causes a resonance change. The lateral size of the artifact is determined by de-convolving a known illumination spot size with the changing resonance characteristics, and the standard scatterer data is selected in conformity with the determined artifact size. The differential analysis using resonance peak shifts corresponding to phase and amplitude information provides an identification algorithm that identifies at least one artifact/material type is identified from matching known behaviors of artifacts/materials.

21 Claims, 7 Drawing Sheets

U.S. PATENT DOCUMENTS 6,717,707 B2 4/2004 Clark
6,778,307 B2 8/2004 Clark
6,879,421 B2 4/2005 Clark et al.
6,927,864 B2 8/2005 Clark et al.
7,022,978 B2 4/2006 Clark et al.
7,102,740 B2 9/2006 Clark et al.

OTHER PUBLICATIONS

U.S. Appl. No. 11/169,517, filed Jun. 29, 2005, Brunfeld, et al.
U.S. Appl. No. 11/149,094, filed Jun. 8, 2005, Toker, et al.
U.S. Appl. No. 11/156,309, filed Jun. 17, 2005, Brunfeld, et al.
U.S. Appl. No. 10/770,866, filed Feb. 4, 2004, Brunfeld, et al.

* cited by examiner

RESONATOR METHOD AND SYSTEM FOR DISTINGUISHING CHARACTERISTICS OF SURFACE FEATURES OR CONTAMINANTS

RELATED APPLICATIONS

This application is related to U.S. Provisional Patent Application "RESONANT DETECTION OF SCATTERING PARTICLES", Ser. No. 60/583,343, filed by the same inventors on Jun. 28, 2004, from which benefit under 35 U.S.C. §119(e) is claimed. This application is also a continuation-in part of U.S. patent application "METHOD AND SYSTEM FOR PERFORMING SWEPT-WAVELENGTH MEASUREMENTS WITHIN AN OPTICAL SYSTEM INCORPORATING A REFERENCE RESONATOR", Ser. No. 10/750,747, filed on Jan. 2, 2004, now U.S. Pat. No. 6,879,421, the specification of which is incorporated herein by reference.

The present application is also related to co-pending U.S. patent applications Ser. No. 11/143,018 entitled "FABRY-PEROT RESONATOR APPARATUS AND METHOD FOR OBSERVING LOW REFLECTIVITY SURFACES", filed on Jun. 1, 2005; Ser. No. 11/149,094 entitled "FABRY-PEROT RESONATOR APPARATUS AND METHOD INCLUDING AN IN-RESONATOR POLARIZING ELEMENT", filed on Jun. 8, 2005; and Ser. No. 11/156,309 "RESONANT ELLIPSOMETER AND METHOD FOR DETERMINING ELLIPSOMETRIC PARAMETERS OF A SURFACE" filed on Jun. 17, 2005, all by the same inventors and assigned to the same Assignee, the specifications of which are incorporated herein by reference.

BACKGROUND OF THE INVENTION

1. Field of the Invention

This invention relates to optical systems, and more specifically, to a resonator-enhanced optical system and method for distinguishing characteristics of artifacts such as surface features or contaminants.

2. Description of the Related Art

Optical systems are often used to provide information about the position, size and characteristics of artifacts such as a feature or "particle" on a surface. Such artifacts may be contaminants such as dust motes on the surface, defects on or in the surface such as inclusions, dislocated or misshapen device elements on a semiconductor wafer or stray material, or the artifacts may actually be features used to encode data or part of the intended surface structure.

The optical characteristics of a surface artifact reveal much about the artifact's nature, shape and size. The artifact may be reflective or absorptive, transmissive (transparent) and may scatter light and/or reflect it back along an incident path, with a corresponding change in phase, amplitude and/or polarization.

At present, only limited possibilities exist for examining a surface to locate defects or other features and determine a type of defects. One instrument that is used in surface inspection systems is a scatterometer, which can provide some scattering profile information for surface artifacts (usually over a few wide angular apertures). However, a scatterometer does not reveal information about the material type of an artifact, only the artifact's scattering profile. Also, a scatterometer also does not typically provide sufficient measurement energy to measure a very small isolated artifact and is typically used more generally to detect, for example, when a surface is contaminated with dust particles. Scatterometers are also insensitive to the height of artifacts as well as the direction of the height variations, but are very sensitive to artifact shape, which severely limits the information they can provide about the material nature of an artifact.

In general, other available systems and techniques that can observe a single artifact and reveal information about the artifact's material composition are very expensive, are typically too slow for a production environment and are generally laboratory instruments with capabilities extending far beyond those needed for the production inspection environment or for data detection applications. Such techniques include Atomic Force Microscopy (AFM), Scanning Tunneling Microscopy (STM) and in-place spectral analysis.

While the powerful range of measurement capability provided by the laboratory instruments mentioned above is not typically needed in a production inspection environment (typically the types of surface artifacts being detected is limited to a fairly small set of possibilities), there is no present alternative for the production inspection environment that provides the ability to distinguish amongst types of artifacts, both with respect to the cost of the instrument and the speed with which a surface can be inspected. For example, it may only be necessary in a particular production environment to determine whether a surface contaminant is dust (a room artifact) or a remnant from a process step (process contamination). If a large quantity of such artifacts are present, a scatterometer will reveal their presence, but not the nature of the artifact material.

The above-incorporated parent U.S. patent application discloses a highly sensitive resonator-enhanced measuring system having a reference resonator, which can be used to provide a relatively low-cost and very high resolution measurement system that can locate variations in surface characteristics such as height and artifact size. The reference resonator system, as well the other systems described in the U.S. patent applications incorporated in the parent application, are suitable for production environments but do not in themselves provide the ability to distinguish the material characteristics of an artifact detected on a surface of interest or examine the relation between the size of an artifact and the artifact's material composition.

Therefore, it would be desirable to provide further refinements in the optical systems described in the above-incorporated parent application and in other optical systems that can distinguish characteristics of an artifact on or in a surface of interest. It would further be desirable to provide such a system that is capable of both locating artifacts and determining their characteristics simultaneously and quickly in a production scanning or data extraction environment.

SUMMARY OF THE INVENTION

The foregoing objectives are achieved in an optical system and method for optical measurement. The measurement system includes an optical illumination system for producing an optical beam, a resonator positioned within a path of the beam and including a surface of interest in a resonant optical path of the resonator, at least one detector for detecting an intensity of light leaving the resonator and a processing system for processing the detected intensity to make determinations of material characteristics of an artifact at (on or in) the surface of interest. The processing system determines or categorizes the material characteristics of an artifact in conformity with the deviation in resonance intensity and position when an artifact is in the path of the beam. A particular material categories or an actual material can be selected by lookup tables or curve matching between known material property effects, the measured effect and a priori information such as possible types of artifact and material.

The processing system compensates for the height of an artifact in the above determination by deconvolving a known illumination spot size from surface measurements, so that the diameter of a spherical scatterer for approximating the optical behavior of the artifact can be determined. Having determined the approximate diameter, expected resonance peak changes for a model scatterer of the same or similar size are compared with the actual peak changes (shift and amplitude reduction) to select one or more candidates for the artifact type/composition.

The model scatterer may be a theoretical model (e.g., a Mie scattering model), a calibrated scatterer such as a latex sphere of known size and material, an interpolation between multiple calibrated scatterers or a scatterer of the nominal surface material. Pattern-matching, interpolative techniques, statistical matching or other mechanisms such as neural networks can be employed to yield a likely material category or material, and confidence levels can be supplied along with a list of likely materials.

The system may include a swept-wavelength optical illumination subsystem, an illumination coupler for producing the above mentioned "measurement" beam and additionally a reference beam from an output of the optical illumination source, a reference resonator for receiving the reference beam, another detector optically coupled to the reference resonator, and a time-domain measurement system coupled to the detectors for comparing detected optical signals received from the detectors, providing a relative measurement capability. In particular, components of a time-domain analysis of the detector outputs provide information about changes in the wavelength of the measurement by using the reference resonator swept-wavelength response in comparison to the measurement resonator response. The measured changes permit determination of variations in the measurement wavelength and/or variations in the measurement resonator, and can be used to provide feedback for adjusting the illumination wavelength or effective cavity length of the measurement resonator or for compensating for the wavelength/resonator changes in the measurement data.

The foregoing and other objects, features, and advantages of the invention will be apparent from the following, more particular, description of the preferred embodiment of the invention, as illustrated in the accompanying drawings.

DESCRIPTION OF EMBODIMENTS OF THE INVENTION

Figure 1:
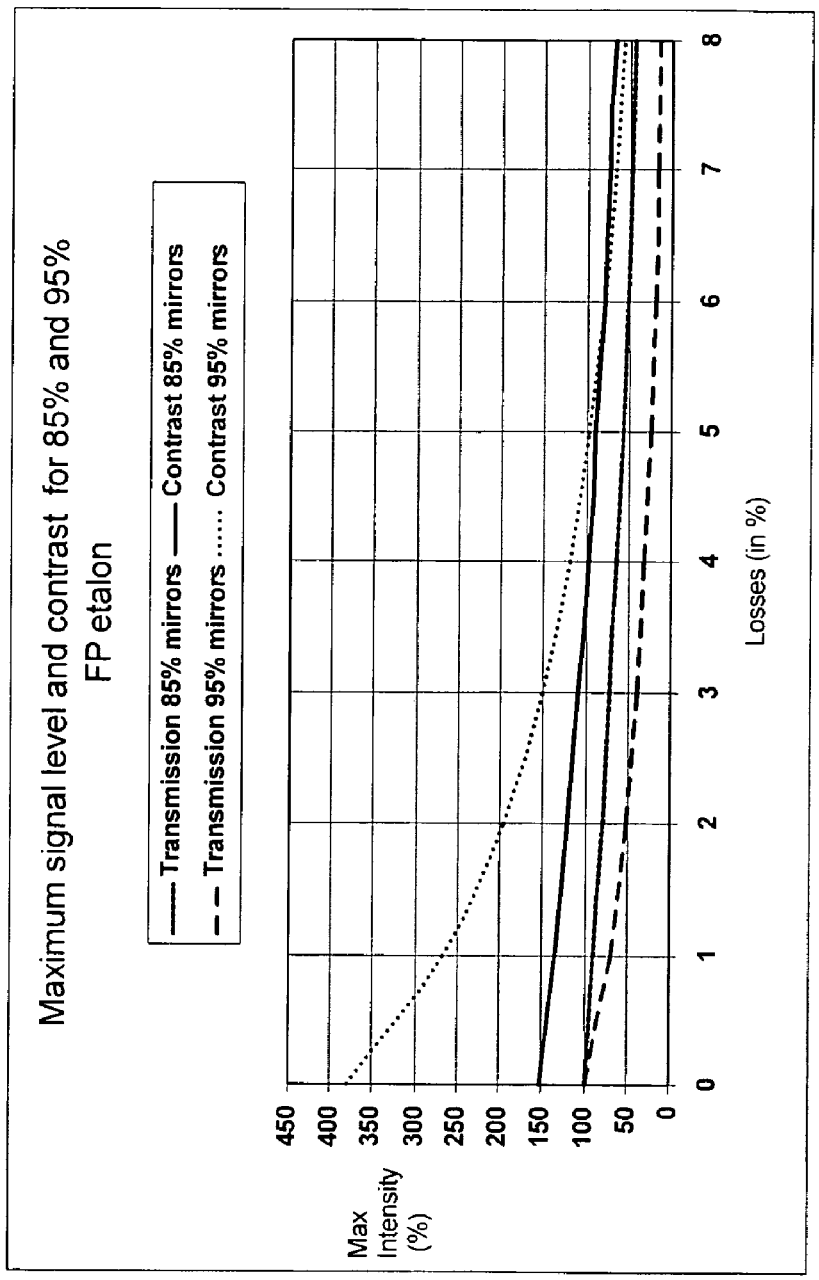
FIG. 1 is a graph depicting performance of a resonator in an optical system in accordance with an embodiment of the present invention.

The above-incorporated parent application describes a dual resonator swept-wavelength technique and system that can be used to improve the performance of various resonator-enhanced optical systems. In general, the parent application, its parent applications and the above-incorporated co-pending U.S. patent applications disclose a variety of techniques and systems using a resonator that enhance the measurement of optical properties of a surface.

However, up to this point, it has not been possible to reliably distinguish between artifact types or between artifacts and surface features for small artifacts disposed on or just below a surface under measurement (surface of interest). While any artifact or feature present on or in a surface of interest will generally change the optical properties of the surface in the region of the artifact, the systems disclosed in the above-incorporated patent applications measure only an intensity profile as the illumination beam is scanned over the surface (or the surface is scanned under the illumination beam). For ellipsometric measurements as described in the above-incorporated co-pending U.S. patent application "RESONANT ELLIPSOMETER AND METHOD FOR DETERMINING ELLIPSOMETRIC PARAMETERS OF A SURFACE", two intensity profiles are obtained. In general, the Fabry-Perot and other resonator systems that are the subject of the above-incorporated patent applications provide surface reflection (or transmission) amplitude information directly from the intensity measurement and surface reflection (or transmission) phase information from the location of the resonance peaks with respect to the wavelength of the illumination and the effective optical length of the resonator cavity.

The characteristics of a surface artifact that affect the reflection are seen as changes in the amplitude and position of the resonance peaks, as well as in the polarization information detected by the above-mentioned ellipsometer. However, if a surface artifact is of different material than the surface or is a speck of or scratch in the same material, as opposed to an ordinary surface variation, a scattering and/or absorptive behavior is included in addition to any variation in height. The present invention provides a method and system that estimate/measure the size of an artifact and use the size to compare the artifact's effect on resonance position and amplitude with that of a model scatterer/absorber. The system makes distinctions based on the resonance changes (peak shift and amplitude change) and the artifact size information to determine material characteristics or categories of artifacts. For example, the present invention can detect a resonance change due to an artifact, and determine whether the artifact is a dust mote, a piece of stray metal or a surface feature. As an alternative to performing a lookup matching that includes the height as a variable, the system can pre-process the detected intensity changes to yield a size-independent material characteristic value (such as estimating n, k for a sphere) and then match those characteristics to determine an artifact type and/or material category.

Referring now to FIG. 1, a graph depicts the behavior of Fabry-Perot resonators of two different efficiencies (mirror reflectivity of 85% and 95%) for transmission peak signal level and contrast (ratio between peak transmission at resonance and minimum background level between resonance peaks). The graph depicts the resonator behavior versus resonator losses (not including the above-stated mirror losses in the loss variable). It is clear that in a resonator with an efficiency above 85%, that very small changes in loss through the resonator can be detected, such as losses introduced by an artifact much smaller than the illumination spot size. The present invention uses those amplitude variations, along with the resonance peak shift information that represents cavity phase changes to determine the characteristics of the material composing an artifact on the surface, or at least a categorization as to material type.

Losses generated by an artifact on or in a reflective surface can be caused by absorption or scattering of light. Apparent losses generated by a transmissive surface measured in a reflection mode can also be due to transmission. In general, most inspection or data detection applications are for reflective/absorptive surfaces and the measurements are made in reflection mode. When transparent surfaces are measured, the measurements can be conducted in transmission and alternatively both in transmission and reflection. Therefore, the above-mentioned absorption or scattering principle for losses still holds true for transparent materials when transmission is measured and reflection losses are either measured or accounted for in the measurement.

The effect of an artifact on the reflection of an illumination spot at a surface can be described by the following equation:

$$\rho_{\mathit{eff}} = (1-\alpha)\rho_2 + \alpha b \rho_{\mathit{def}} e^{i\delta}$$

in which $\alpha$ is the ratio of the defect area to the illumination spot area, $\rho_2$ is the ideal surface reflectivity magnitude, $\rho_{\mathit{def}}$ is the averaged reflectivity magnitude for the defect, b is the fraction of the light reflected by the defect into the field of the lens if a lens is employed. Finally, $\delta = 4\pi h/\lambda$, where $\lambda$ is the wavelength and h is the physical defect height. It is useful to rewrite the above expression in the form $\rho_{\mathit{eff}} = |\rho_{\mathit{eff}}| \cdot e^{i\delta_{\mathit{eff}}}$ so that the effective reflectivity when the spot is over the artifact is expressed as an amplitude modification and a phase modification. The absolute reflectivity $|\rho_{\mathit{eff}}|$ is determined in the present invention from the resonance peak intensity when scanning over the defect, whereas the phase $\delta_{\mathit{eff}}$ corresponds to the shift of the resonance peak(s).

Given the two equations above, the absolute reflectivity and phase can be expressed as an expansion. For instance, if $\rho_{\mathit{def}}$ is real, then:

$$\rho_{\mathit{eff}} = \rho_2\left\{(1-\alpha) + \alpha b \frac{\rho_{\mathit{def}}}{\rho_2} e^{i\delta}\right\}$$

$$= \rho_2\left\{1 - \alpha + \alpha b \frac{\rho_{\mathit{def}}}{\rho_2}\cos\delta + i \cdot \alpha b \frac{\rho_{\mathit{def}}}{\rho_2}\sin\delta\right\}$$

and $$|\rho_{\mathit{eff}}| = \sqrt{\left(1 - \alpha + \alpha b \frac{\rho_{\mathit{def}}}{\rho_2}\cos\delta\right)^2 + \left(\alpha b \frac{\rho_{\mathit{def}}}{\rho_2}\sin\delta\right)^2}$$

$$\tan\delta_{\mathit{eff}} = \frac{\alpha b \frac{\rho_{\mathit{def}}}{\rho_2}\sin\delta}{1 - \alpha + \alpha b \frac{\rho_{\mathit{def}}}{\rho_2}\cos\delta}$$

For small defects ($\alpha \ll 1$, $\delta \ll 1$) of the same material as the surface, i.e., $\rho_{\mathit{def}} = \rho_2$, the effective phase (and effectively the observed height) is proportional to the defect phase $\delta$ multiplied by the defect area $\alpha$ and taking losses into account, the following approximation will hold:

$$\tan\delta_{\mathit{eff}} = \alpha b \frac{\rho_{\mathit{def}}}{\rho_2}\delta = \alpha b \delta$$

In the presence of scattering losses, the observed resonance peak shift is smaller. If the defect material is different, then reflection phase carries an additional proportionality coefficient equal to the ratio of the two reflectivities, as in the middle expression in the above-stated approximation. In the general case, the defect reflectivity $\rho_{\mathit{def}}$ relative to the surface reflectivity $\rho_2$ is a complex number, and the expansion and approximation above must be modified accordingly. However, in general, the observed "height" (i.e., the shift of the resonance peak(s)) includes effects of both the geometry (essentially the local height) and the material of the surface. The changes in the maximum signal at the resonance peak include effects of both scattering losses caused by the artifact and losses introduced by absorption in the material.

Figure 2A:
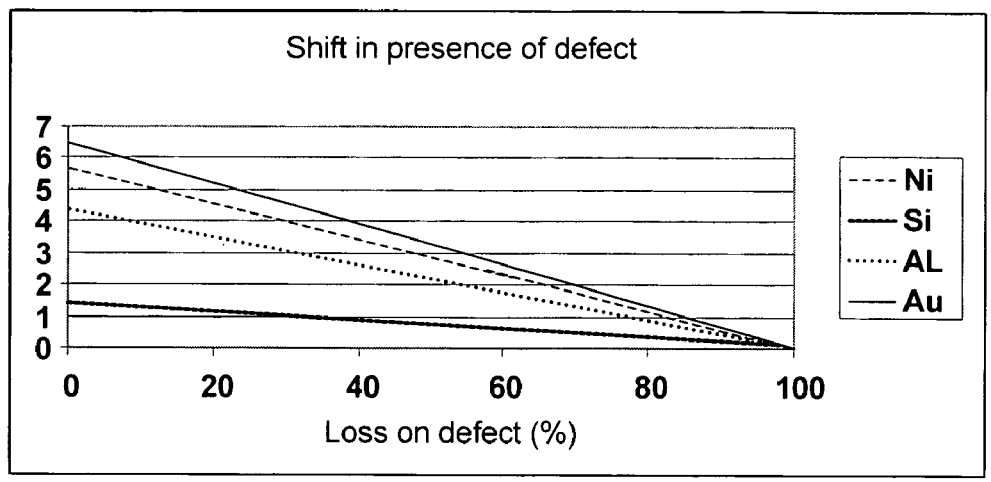
FIGS. 2A and 2B are graphs depicting resonator detected characteristics in an optical system in accordance with an embodiment of the present invention.
Figure 2B:
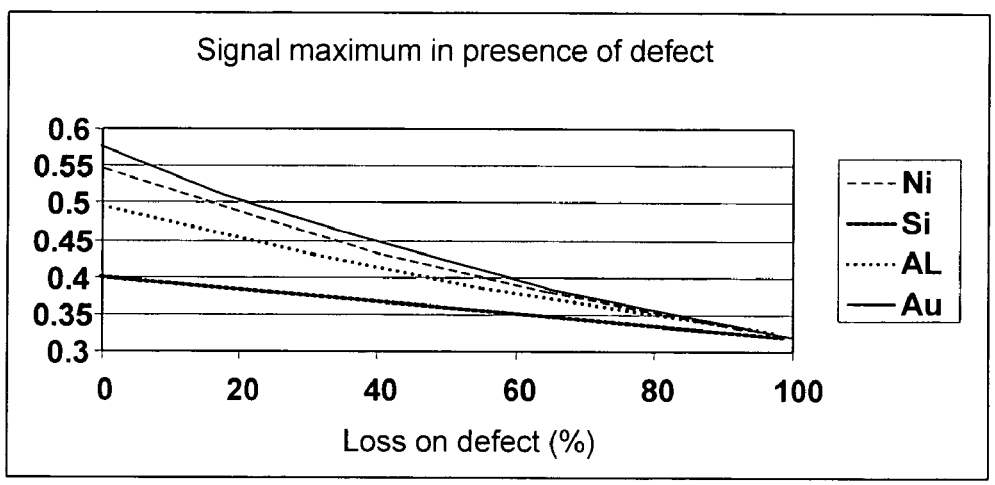

Referring now to FIGS. 2A and 2B, the effects of cavity losses on resonance peak shift and resonance peak amplitude, respectively, are shown for a variety of defect materials. The base substrate is Nickel, so the graphs are illustrative of defects or features that are of the same material (e.g., "pits" or "bumps") and defects or features that are of another material (e.g., stray material or impurities in the substrate). Defects that are of the same material are essentially local height changes and are measured by the systems disclosed in the above-incorporated patent applications and U.S. Pat. Nos. 6,653,649, 6,714,295, 6,717,707 and 6,778,307 issued to Applicant Clark and others.

The present invention addresses an arbitrary and new case of a defect of both unknown and general size and material. The above-referenced figures provide the basis for an exemplary illustration of how material properties are detected in the present invention. In essence, the system of the present invention measures the size of an artifact, and matches the resonance peak shift and amplitude decrease with that of a model artifact of the same or similar size to the artifact. While the present invention will not always provide a unique solution for all materials, as the defect shape (e.g., inclination) will affect the loss on the defect and some materials may be closely matched in characteristics, in general, inspection systems, data storage systems and other similar optical systems are faced with the challenge of recognizing a finite and relatively small set of materials and artifact types, which can be matched from a known database of artifact materials and expected height, size and/or location.

Using the ellipsometric or polarimetric techniques disclosed in the above-incorporated U.S. patent application "RESONANT ELLIPSOMETER AND METHOD FOR DETERMINING ELLIPSOMETRIC PARAMETERS OF A SURFACE", in the context of the present invention can provide additional inputs to a matching or "material fitting" algorithm. The polarization information provided by the above-mentioned techniques improve accuracy in determining or categorizing artifacts. The algorithms used to match or fit knowledge of material optical properties to measurements are disclosed herein as programmatic constructs for execution in a general or special purpose computer system, but can alternatively be implemented in neural networks, genetic algorithms, and statistical or deterministic pattern matching algorithms such as are well known in the field of image recognition and other data analysis arts.

Figure 3:
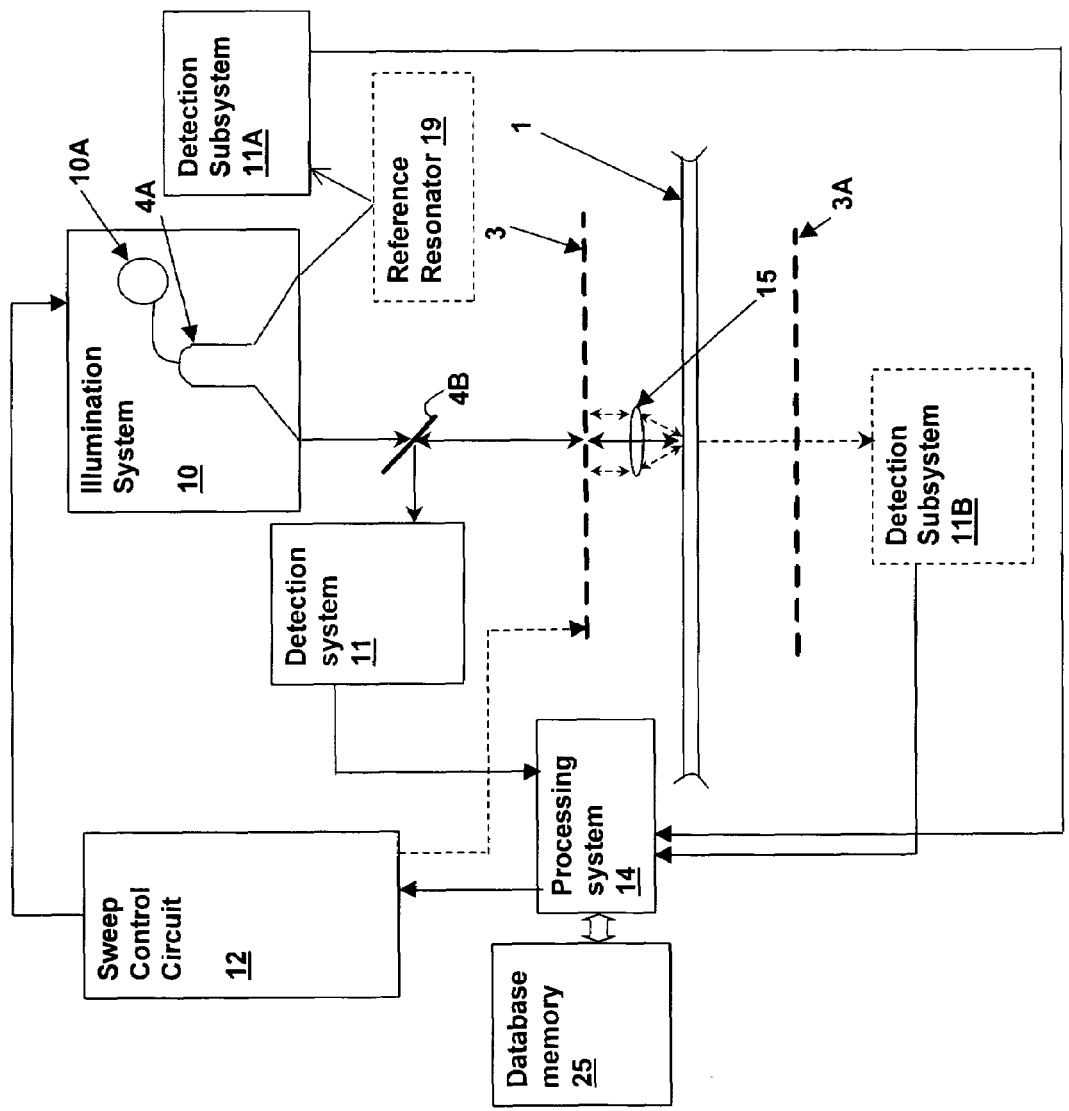
FIG. 3 is an illustration depicting an optical system in accordance with an embodiment of the present invention.

With reference now to the figures, and in particular to FIG. 3, an optical system in accordance with an embodiment of the invention is depicted. An optical illumination system 10 includes an illumination source 10A that is swept in wavelength under the control of sweep control 12, that may in turn be controlled by a processing system 14. Processing system 14 controls the operation of the optical system depicted, which is generally in the form of a resonator-enhanced inspection or data detection system. Illumination source 10 will generally be a laser diode having a tunable cavity, but other sweepable illumination sources may be used such as broadband lasers having tunable optical filters for sweeping the filter passband to yield a swept-wavelength illumination subsystem. A coupler 4A divides the output of illumination source 10A into a reference beam and a measurement beam. The measurement beam is introduced to a measurement resonator formed between a partially reflective surface 3 and a surface of interest 1 via a beamsplitter 4B that returns light reflected from the measurement resonator to a detection system 11 that provides input to the artifact-detection algorithm of the present invention executing within processing system 14, which may be a general-purpose computer system such as a mainframe or personal computer system, or a special purpose instrument computer system. The reference beam is provided to a reference resonator 19 the output of which is provided to a detection system 11A that provides a reference output to processing system 14 by which variations in the measurement resonator can be determined by comparison rather than relying solely on the linearity of the wavelength sweep, and intensity and wavelength stability of illumination source 10A.

A database memory 25 is coupled to (or included within) processing system 14. Database memory represents information, statistics or algorithms that identify material, material category and/or artifact category optical characteristics for matching with results of the measurements in the depicted system and can be raw matching data, such as resonance peak displacement and amplitude factors such as those described above, or more abstract information such as n, k parameters used in matching computations. Alternatively, with respect to abstract mathematical models, neural networks and similar decision-making processes, database 25 may not contain discrete data at all, but may rather represent an algorithm having inherent "data" at its core. For example, a "black box" neural network or statistical algorithm could accept defect size, resonance peak amplitude and peak shift for a given artifact and render an output as a list of likely materials (or material categories) and confidence levels.

The measurement resonator optionally includes a lens 15 that images surface of interest 1 onto partially reflective surface 3 and vice-versa to increase the resolution of the system. optionally, as an alternative to tuning the illumination wavelength or in concert with wavelength tuning or sweeping, sweep control circuit 12 can mechanically move partially reflective surface 3 or tune the cavity formed between partially reflective surface 3 and surface of interest 1 via an electrically refractive-tunable element or motor such as a piezoelectric element or voice-coil.

Also optionally shown, is a detection subsystem 11B that detects light transmitted through surface of interest 1 and an optional second partially reflective surface 3A that may be included to support resonance. When partially reflective surface 3A is not present but detection subsystem 11B is and surface of interest 1 is a surface of a transparent material, then measurements can be made of light transmitted by the resonator and used to further distinguish between material properties by determining a transmitted intensity in addition to the reflected intensity from the resonator cavity. If partially reflective surface 3A is included, then resonance is supported between partially reflective surfaces 3A and 3. In the above-mentioned configuration, surface of interest 1 can be on a completely or partially transparent material and inspected for defects such as impurities, scratches or other scattering or absorbing artifacts and the resulting resonance behavior observed at detection system 11 and optionally detection system 11B. (Note that partially reflective surface 3A can be totally reflective if detection subsystem 11B is not employed.)

Reference resonator 19 can be a very stable resonator, as no moving parts or tunability is required for the reference resonator R1. Either measuring or reference resonator may be a Fabry-Perot resonator, or one may be Fabry-Perot and the other another form of resonator. As reference resonator 19 does not require tuning or scanning, it may be made from temperature stable materials in a solid housing and the size of resonator 19 may not be a critical factor, permitting mounting of reference resonator 19 outside of a scanning head that includes partially reflective surface 3.

Figure 4:
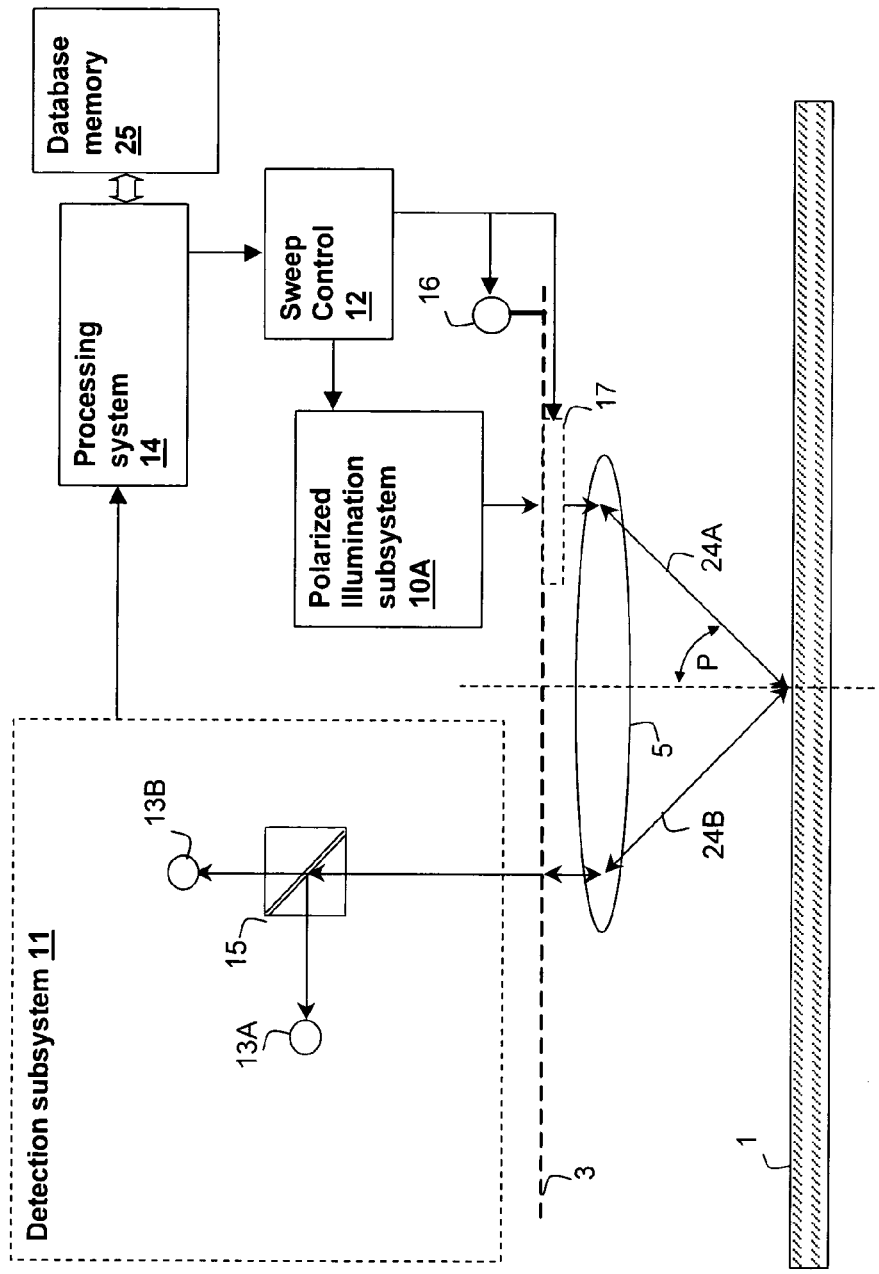
FIG. 4 is an illustration depicting another optical system in accordance with an embodiment of the present invention.

Referring now to FIG. 4, an optical schematic of an optical system in accordance with another embodiment of the invention is illustrated. The system illustrated is a resonant ellipsometer based on a dual reflector Fabry-Perot resonator, but will also be used to illustrate non-normal incidence Fabry-Perot resonators in general, and it should be understood that the present invention may employ non-normal incidence detection without requiring polarimetry or ellipsometry as part of the measurement system. In the depicted embodiment, one partially reflective surface 3 provides a first reflector and surface of interest 1 provides the other reflector. However, the resonant path terminates only on partially reflective surface 3 at two distinct locations for each ray, with surface of interest 1 as an intermediate point on the path, which effectively doubles the sensitivity of the system to changes in surface of interest 1. The above is accomplished by incorporating a direction changing element (which can alternatively be replaced with two discrete direction-changing single elements) that has a direction-changing characteristic on either side of the point of intersection of rays 24A and 24B with surface of interest 1. A high numerical aperture (high-NA) lens 5 provides the direction-changing element of the depicted embodiment, but other configurations and elements may be substituted as disclosed in the above-referenced U.S. patent applications can be used as well.

Lens 5 alters the angular direction of light leaving and striking partially reflective surface 3 from normal incidence at partially reflective surface 3, to an angle P away from normal, so that surface of interest 1 is intersected by rays 24A and 24B at a predetermined angle other than normal. Polarized light is provided by a polarized illumination subsystem 10A, and is reflected from surface of interest 1 at the non-normal incidence angle P. The wavelength of the illumination is swept by sweep control circuit 12 controlled by processor 14 that also receives outputs of detection subsystem 11 that determines the polarization changes occurring along the resonance path including rays 24A and 24B.

Tuning of the effective cavity length can accomplished by one of three illustrated options, as mentioned above with respect to FIG. 2, and as further detailed below. In the first, the illumination source is tuned or swept. Sweep control 12 provides a tuning signal synchronized in timing with processor 14 to polarized illumination subsystem 10A. The illumination element may be a semiconductor or tuned-cavity laser. Suitable types of lasers are tunable external cavity lasers (ECL), distributed-feedback (DFB) lasers, distributed Bragg reflector (DBR) lasers and vertical cavity surface emitting lasers (VCSEL). In the second option, the cavity itself is tuned via an electromechanical system that moves one of the resonator reflectors. In the illustrated option, a electro-mechanical element 16 such as a piezo-electric crystal/ceramic element or an electromagnetic "voicecoil" or other means is employed to move partially reflective surface 3 to either tune to a resonance peak (via feedback from processor 14) or to sweep through a range of cavity lengths. The third illustrated option is to tune the cavity with an electro-optical element 17 that has electrically tunable optical or mechanical properties. By changing the thickness or refractive index of a material (e.g. an electro-optical liquid or crystal) with an applied voltage, the effective cavity length of the resonator can be tuned or swept.

Detection subsystem 11 is a standard orthogonal polarization detector. A polarizing beam splitter 15 splits the beam transmitted through partially reflective surface 3 at the transmission end of the resonator. The resulting beams (generally representing s and p polarizations) are then provided to individual detectors 13A–B that may be a single point detector such as a photodiode, or may be part of an array such as a CMOS or CCD sensor. The above-incorporated U.S. patent application "RESONANT ELLIPSOMETER AND METHOD FOR DETERMINING ELLIPSOMETRIC PARAMETERS OF A SURFACE" describes how resonance peaks can be observed in each polarization to determine the ellipsometric or polarimetric parameters of surface of interest 1. By extension, the ellipsometric parameters of artifacts on surface of interest will provide partial polarizing effects that can be observed in the output of detectors 13A and 13B and used to further classify an artifact. For example, a dust mote will be an almost 100% depolarizer, while a metallic artifact will have a polarizing effect that depends primarily on its shape and any Brewster region with respect to the angle of incidence. A refractive artifact will have a polarizing effect that depends on the angle of incidence with respect to the Brewster angle.

Figure 5:
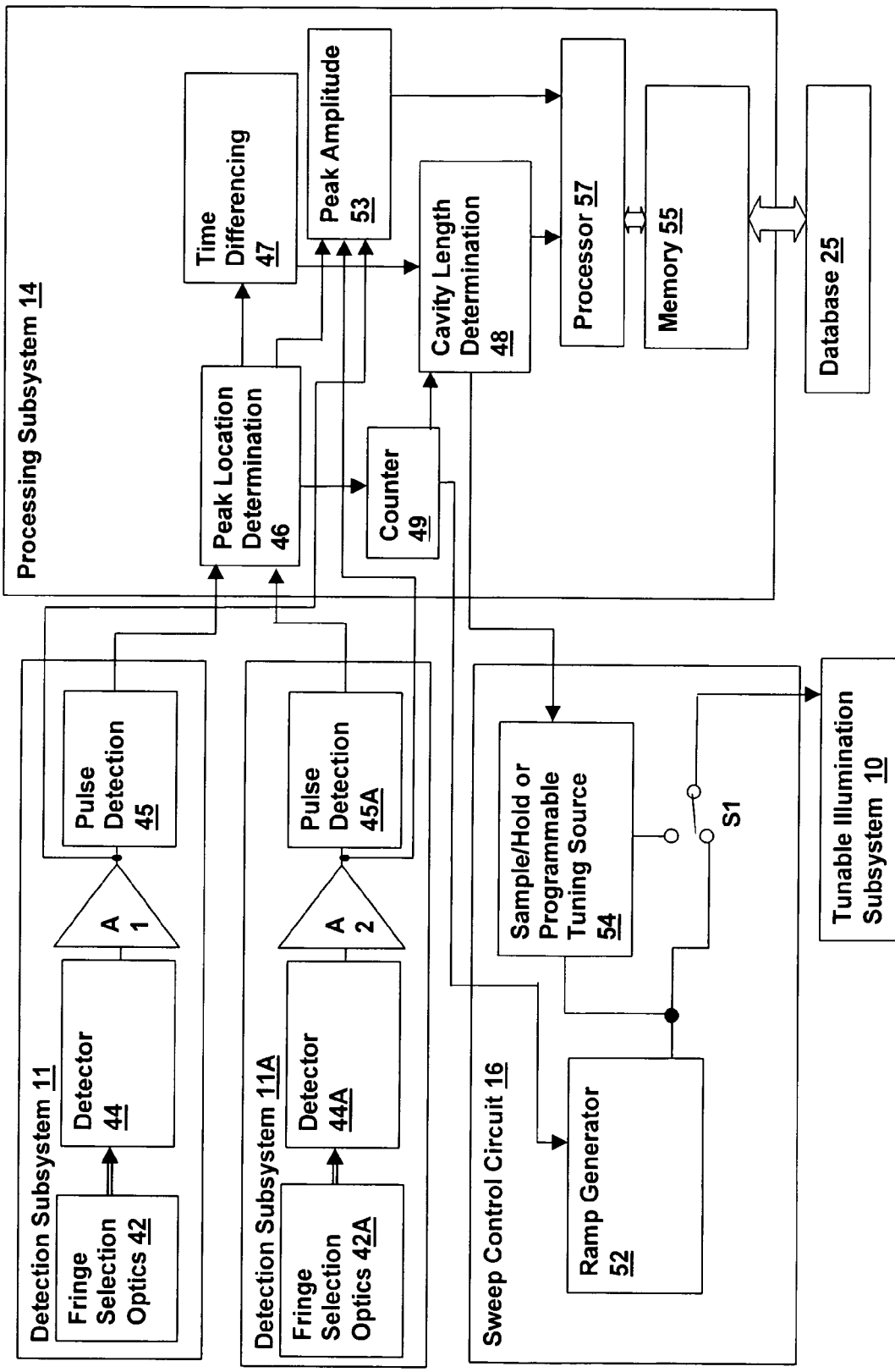
FIG. 5 is a block diagram showing details within the optical system of FIGS. 3 and 4.

Referring now to FIG. 5, details of the detection and processing systems in accordance with embodiments of the present invention are depicted. Detection subsystems 11 and 11A include fringe selection optics 42 and 42A that select the interferometric detection point as the output to detectors 44 and 44A. Amplifiers A1 and A2 adjust the gain and offset of detector 44 and 44A outputs to provide a control signal to pulse detection circuits 45 and 45A. Pulse detection circuits 45 and 45A are designed to match the shape of the pulses received by detection subsystems 11 and 11A, which will generally follow the shape of the Airy-function (for a linearly changing illumination wavelength) that describes the characteristic response of the resonator as shown in FIG. 4. Pulse detection circuits 45 and 45A may employ matched filters or other correlation blocks, in order to maximize the received signal-to-noise ratio in conformity with a predictable pulse shape.

The outputs of detection subsystems 11 and 11A enter peak location determination block 46 within processing subsystem 14. Peak location determination block 46 determines a time relationship of resonance peaks occurring in the measurement resonator and reference resonator 19 as the wavelength of illumination subsystem 11 is swept in swept-wavelength mode. Peak location determination block may be a threshold comparator, but preferably a partial response detector or other precision pulse position estimation circuit having a characteristic suitably matched to the output of pulse detection circuits 45 and 45A.

A peak amplitude detector 53 takes the output of the measurement amplifier A1 at the peak, as well as the output of reference amplifier A2, so that the maximum intensities can be determined for each resonance peak. Processor 57 can then note the peak amplitude and the peak positions to determine changes due to artifacts on surface of interest 1. Time differencing block 47 determines the differences between the resonance peaks for each detection subsystem 11 and 11A so that a cavity length determination block 48 can extract a cavity length change for the measurement resonator relative to reference resonator 19. By comparing the measured cavity length to the known cavity length of reference resonator 19, the wavelength deviation can be established and used to correct the response of detection subsystem 11, improving the resolution and accuracy of the measurement.

The corrected measurement resonator cavity length change information is used by processor 57 along with the peak amplitude information from peak amplitude measurement block 53, which may provide raw or ratiometric intensity data from the measurement detectors and reference detectors (as well as polarization detectors 13A–B when ellipsometry or polarimetry is further employed).

If the sweep range covers more than one resonance peak, a counter 49 is used to count the number of resonance points scanned through by the swept illumination wavelength and can be used to reset ramp generator 52 within sweep control circuit 16. Counter 49 can thus ensure that a constant number of resonance points is scanned in a time interval or per measurement.

As an alternative to direct measurement output from processing subsystem 14 while illumination subsystem 11 is in swept-wavelength mode, a sample/hold or programmable tuning source 54 may be used to provide a constant-wavelength mode for illumination source 10. A switch S1 provides selection of constant-wavelength mode vs. swept-wavelength mode and sample/hold may be used to sample a particular point in the ramp generator 52 sweep output corresponding to a particular resonance operating point of reference resonator 19 (not necessarily a resonance peak) or the wavelength of illumination subsystem 10 may be programmed via a programmable register, divider, divider/multiplier loop or other means. Such a configuration provides open-loop control of the operating wavelength of tunable illumination source 11 while in constant-wavelength mode, but representing a highly accurate wavelength as determined by the response of reference resonator 19.

In general, all of the processing functions post analog amplification and conversion can be performed by processor 57, but for high-speed systems, it may be desirable to perform functions such as conversion of resonance peak positions to timing information via analog filters and correlators, as depicted. It may further be desirable to integrate over multiple sweeps more quickly than processor 57 would allow if directly involved in each measurement. Therefore it should be understood that as to the input parameters: resonance peak amplitudes, changes in peak positions, and optionally differences between the two for orthogonal polarizations, can be obtained by sampling, integration or other means, and the present invention primarily concerns the use of that information in an algorithm or processing block that determines the material characteristics or category of an artifact from the input optical measurement parameters described above.

Further, the values in database 25 may represent differences between resonance peak changes for possible artifact materials versus those for standard scatterers (of one or more sizes) that are calibrated to the system, such as latex spheres that are measured by the system in a calibration process. Alternatively, or in combination, the values in database 25 may represent differences in resonance peak changes between different sized scatterers of the same material as the surface and scatterers of differing material.

Figure 6:
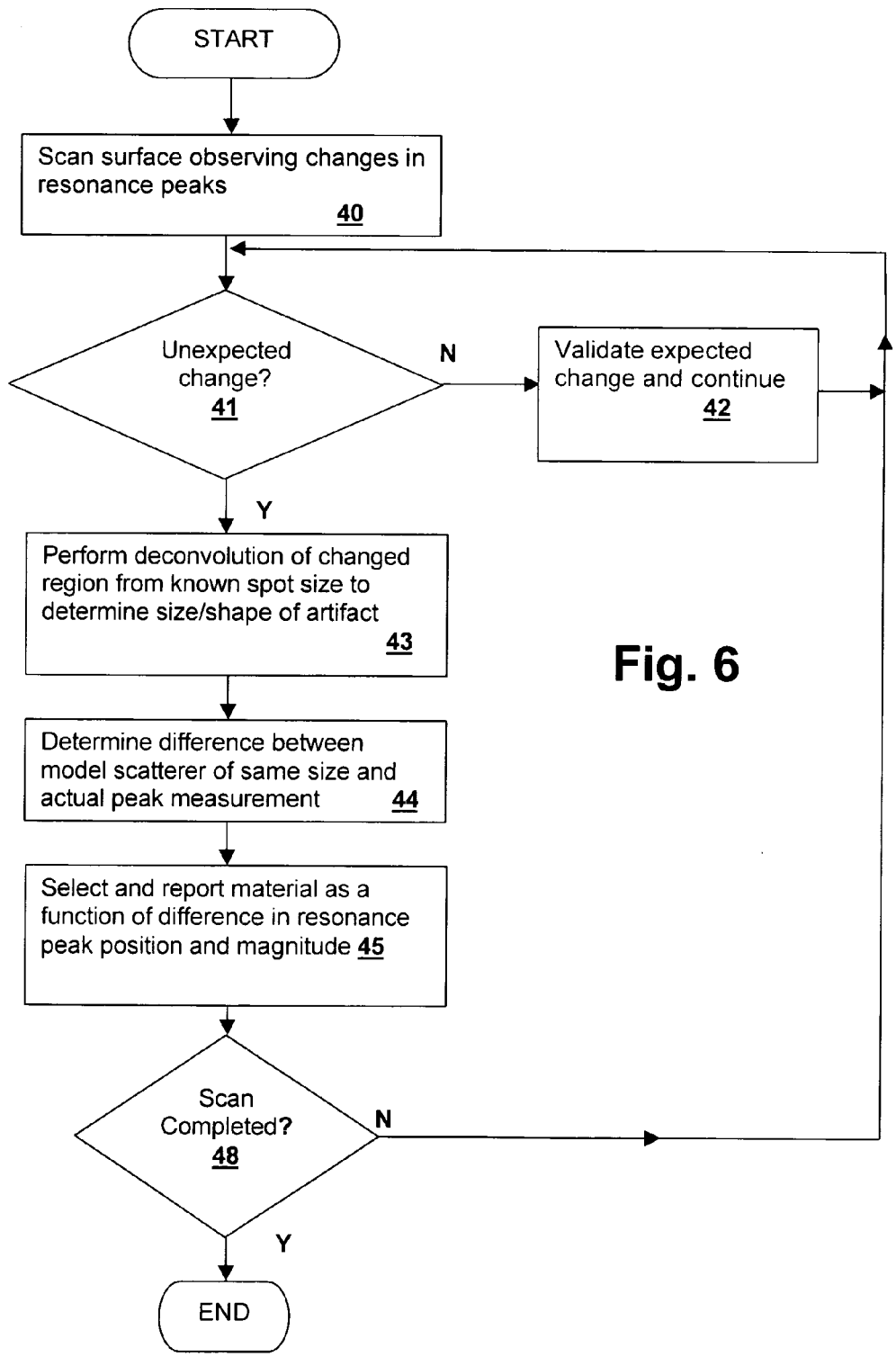
FIG. 6 is a flowchart depicting a method in accordance with an embodiment of the present invention.

Referring now to FIG. 6, a method in accordance with an embodiment of the present invention is depicted in a flowchart. First, the surface is scanned and changes in the resonance peaks are observed (step 40). If an unexpected change occurs (decision 41) then an artifact has been detected, otherwise, any expected change is validated and scanning continues (step 42). Next, if an unexpected change in the resonance peaks occurred (decision 41), then a deconvolution of the change region is performed knowing the exact size and shape of the spot in order to determine the size and shape of the artifact (step 43). The average width (or other determined dimensional characteristics) is used to select resonance peak change information for a standard scatterer (step 44), and then a material category or actual material is selected and reported as a function of the differences between measured resonance peak position and magnitude changes and expected changes for the standard scatterer (step 45), optionally including measurements in two orthogonal polarizations as part of the input for the material selection. Until scanning is completed (step 48), steps 40–45 are repeated.

With respect to estimating the size of an artifact, if the artifact is large with respect to the spot size or of the same order, then the size of the artifact can be easily estimated as the spot is scanned over the artifact. However, if the artifact is small compared to the spot size, then the deconvolution of the spot size from the artifact's image is subject to more error. In such cases, the calibration of the system with latex spheres or other calibration artifacts is desirable to improve the accuracy of the system. In either case, the centroid of the spot should be known with a high degree of accuracy so that the changes in the projection of the artifact into the illumination spot can be accurately observed as the surface is scanned.

Figure 7:
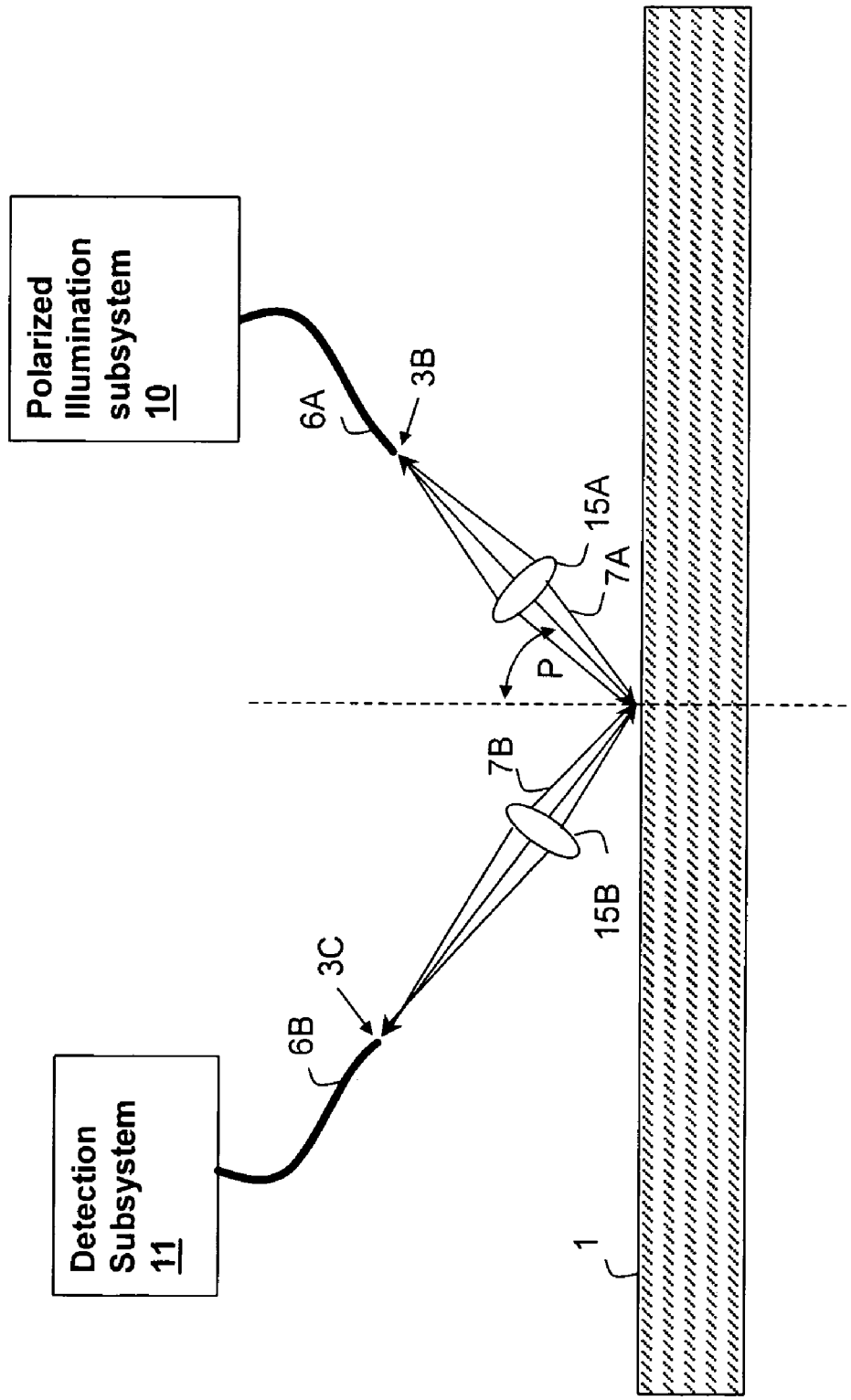
FIG. 7 is an illustration depicting another optical system in accordance with an embodiment of the present invention.

Referring now to FIG. 7, an optical system in accordance with another embodiment of the present invention is depicted. The system of FIG. 7 is illustrative of a system in which a point illumination source and a point detector are imaged onto surface of interest 1 by a pair of imaging lenses 5A and 5B (finite conjugation ratio) focused on surface of interest at an angle of incidence other than normal. The point source and point detectors can be provided, as shown, by a pair of optical fibers 6A, 6B that couple their respective subsystem (polarized illumination subsystem 10 and detection subsystem 11) directly to the measurement resonator. A polarizing splitter may be included in detection subsystem 11 and polarization-preserving optical fibers 6A, 6B can be used to provide the additional ellipsometric artifact information by implementing an ellipsometer.

Optical fibers 6A, 6B have distal ends polished and coated with a partially reflective coating, so that the Fabry-Perot resonator is formed between the partially reflective faces 3B, 3C at the distal ends of optical fibers 6A, 6B. Imaging beams 7A and 7B intersect at a point on surface of interest 1 for which the length is resonant. Any misalignment of the focal axes of imaging lenses 5A and 5B, results only in a shift of the point of intersection of beams 7A and 7B to a point where the resonance is supported, providing very robust operation.

Illumination subsystem 10 provides an optical source to illuminate surface of interest 1 through resonator and detection subsystem 11 provides a detection mechanism to detect changes in intensity of light leaving the resonator, whereby features of surface of interest 1 are measured. Focusing elements 5A, 5B described in the above-incorporated co-pending patent applications are included to focus the light traveling along the resonant paths onto surface of interest 1 to improve the performance of the resonator by de-sensitizing the resonator to angular errors with respect to surface of interest 1.

While the point source/point detector embodiment has disadvantages in that the mirror (fiber end) quality must be very high, the use of such a system is very advantageous in that no collimator is required to produce a small spot size, no separate mirrors are required to form the Fabry-Perot resonator, thus reducing the number of positioning variables in the system. The reduction in complexity and weight is also advantageous for scanning and data storage/retrieval device applications.

It should be understood that in all embodiments of the invention employing a polarized illumination source and a detector to detect ellipsometric parameters of artifacts on surface of interest 1, that polarization preserving optics should be employed throughout the measurement path, or the polarization of the elements must be taken into account in the measurement and/or subsequent data analysis.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. An optical system, comprising:
   an illumination system for providing an illumination beam for illuminating a surface of interest through a first partially reflective surface;
   at least one reflector including said first partially reflective surface for sustaining multiple internal reflections in a resonant cavity formed at least partially between said at least one reflector and said surface of interest, and wherein an extraction partially-reflective one of said at least one reflector permits light to exit said resonant cavity;
   a detector for detecting an intensity of light leaving said cavity through said extraction reflector;
   a scanning system for moving one of said illumination beam and said surface of interest to generate a relative movement between said surface of interest and said illumination beam; and
   a processing system having an input coupled to said detector for identifying at least one material type of an artifact disposed at said surface of interest from a change in a resonance position and amplitude of said detected intensity caused by said relative movement across said artifact.

2. The optical system of claim 1, wherein said optical illumination system has a variable wavelength, and wherein said processor detects said change in resonance position by detecting resonance peaks occurring at distinct values of said variable wavelength and detects said change in amplitude by detecting said intensity of said light leaving said cavity at said resonance peaks.

3. The optical system of claim 2 wherein said optical illumination system has a swept wavelength, and wherein said processor detects said resonance peaks and stores timing information associated with said resonance peaks, whereby a difference in illumination wavelength corresponding to said resonance peaks is determined, and wherein said processing system determines said change in resonance position from said timing information.

4. The optical system of claim 1, wherein said resonant cavity has a tunable cavity length, and wherein said processor detects said change in resonance position by detecting resonance peaks occurring at distinct values of said tunable cavity length and detects said change in amplitude by detecting said intensity of said light leaving said cavity at said resonance peaks.

5. The optical system of claim 1, wherein said processing system compares said change in resonance position and amplitude with predetermined values and determines a type of said artifact in conformity with a result of said comparison.

6. The optical system of claim 1, wherein said processing system further determines a size of said artifact by performing a deconvolution of a predetermined spot size of said multiple internal reflections incident upon said surface of interest from changes in said detected intensity caused by said artifact as said scanning system generates said relative motion across said artifact.

7. The optical system of claim 6, wherein said processing system further performs said identifying in conformity with predetermined resonance peak changes for a standard scatterer model selected in conformity with said determined size.

8. The optical system of claim 7, wherein said processing computes differences in an expected resonance peak shift and an expected resonance peak amplitude change for said selected scatterer model and a measured resonance peak shift and a measured resonance peak amplitude change, and wherein said identifying is performed in conformity with said computed differences.

9. The optical system of claim 7, wherein said standard scatterer model is a set of values for a calibrated scatterer and wherein said predetermined resonance peak changes are obtained by performing a calibration with said calibrated scatter.

10. The optical system of claim 1, further comprising:
an optical coupler for receiving an output of said illumination system, and wherein said resonator is a measurement resonator coupled to a first output of said optical coupler;
a reference resonator coupled to a second output of said optical coupler for generating at least a second resonance within a path of said reference beam; and
at reference detector coupled to said reference resonator for measuring a reference intensity of light at an associated one of said at least one reference resonator, and wherein said processing system is further coupled to an output of said reference detector, and compensates for variations in said detected intensity from said cavity due to changes in effective length of said cavity and a wavelength of said illumination system in conformity with variations in said reference intensity.

11. The optical system of claim 1, wherein said illumination beam and said multiple internal reflections illuminate said surface of interest along an incidence angle away from normal in a resonant path of said cavity.

12. The optical system of claim 11, wherein said illumination system provides a polarized illumination beam, and wherein said detector further comprises:
a polarizing beam splitter for splitting said light leaving said cavity into two output beams having different polarizations; and
two intensity detectors, each coupled to one of said output beams, and wherein said processing system computes polarizing characteristics of said artifact and said surface of interest at an intersection of said resonant path and said surface of interest in conformity with intensity outputs of said at least two detectors to determine changes in polarizing amplitude characteristics introduced by said artifact.

13. The optical system of claim 12, wherein said processing system further determines changes in said resonance position for each of said intensity outputs, and determines a polarizing phase relationship of said artifact from changes in resonance position as a wavelength of said illumination beam is changed.

14. The optical system of claim 12, wherein said processing system further determines changes in said resonance position for each of said intensity outputs, and determines a polarizing phase relationship of said artifact from changes in resonance position as an optical length of said cavity is changed.

15. A method of detecting optical characteristics of an artifact disposed at a surface of interest, said method comprising:
repeatedly reflecting incident light in a cavity formed at least partially between at least one reflector including at least one partially reflective surface and a surface of interest;
detecting an intensity of light transmitted from said cavity through said at least one partially reflective surface;
moving one of said surface of interest and said at least incident light to generate a relative motion of said surface of interest with respect to said incident light;
changing an effective optical length of said cavity through a range of said effective optical length, at positions of said moving, whereby a range of said effective optical length can be studied at each of said positions; and
identifying at least one material type of said artifact from changes in a resonant effective optical length of said cavity and a magnitude of said intensity to values taken when said moving has located said incident light on said artifact from values taken when said moving has located said incident light on surface of interest away from said artifact.

16. The method of claim 15, wherein said changing changes a wavelength of said incident light.

17. The method of claim 15, wherein said changing changes an optical length of said cavity.

18. The method of claim 15, further comprising matching said changes in a resonant effective optical length of said cavity and said magnitude of said intensity with predetermined optical characteristics to determine a type of said artifact.

19. The method of claim 15, further comprising deconvolving a spot size of said incident light from a profile of said artifact as said moving is performed by processing said detected intensity to determine a width of said artifact.

20. The method of claim 15, wherein said incident light is polarized light and wherein said repeatedly reflecting incident light is performed at a non-normal angle at said surface of interest, wherein said method further comprises splitting said transmitted light into two beams representing different polarizations of said incident light, wherein said detecting detects intensities of both of said two beams, and wherein said computing further computes polarizing characteristics of said artifact from changes in a resonant effective optical length of said cavity and a magnitude of said intensity with respect to both of said beams.

21. An optical system, comprising:
- an illumination system for providing an illumination beam for illuminating a surface of interest through a first partially reflective surface;
- at least one reflector including said first partially reflective surface for sustaining multiple internal reflections in a resonant cavity formed at least partially between said at least one reflector and said surface of interest, and wherein an extraction partially-reflective one of said at least one reflector permits light to exit said resonant cavity; and
- means for identifying at least one material type of an artifact disposed on said surface of interest in conformity with a detected intensity of said light exiting said cavity.

\* \* \* \* \*